United States Patent
Bencini et al.

(10) Patent No.: US 10,329,216 B2
(45) Date of Patent: Jun. 25, 2019

(54) CATALYTIC COMPOSITION AND PROCESS USING IT FOR THE ALKYLATION OF AROMATIC HYDROCARBONS WITH ALCOHOLS, OR MIXTURES OF ALCOHOLS AND OLEFINS

(71) Applicant: versalis S.p.A., San Donato Milanese (MI) (IT)

(72) Inventors: Elena Bencini, Borgo Virgilio (IT); Giovanni Antonio Fois, Borgo Virgilio (IT); Roberto Buzzoni, Chivasso (IT)

(73) Assignee: versalis S.p.A., San Donato Milanese (MI) (IT)

( * ) Notice: Subject to any disclaimer, the term of this patent is extended or adjusted under 35 U.S.C. 154(b) by 225 days.

(21) Appl. No.: 15/026,924

(22) PCT Filed: Oct. 14, 2014

(86) PCT No.: PCT/IB2014/065296
§ 371 (c)(1),
(2) Date: Apr. 1, 2016

(87) PCT Pub. No.: WO2015/056167
PCT Pub. Date: Apr. 23, 2015

(65) Prior Publication Data
US 2016/0297728 A1    Oct. 13, 2016

(30) Foreign Application Priority Data
Oct. 15, 2013  (IT) .............. MI2013A1704

(51) Int. Cl.
*C07C 2/66* (2006.01)
*C07C 2/86* (2006.01)
*B01J 29/70* (2006.01)
*B01J 35/10* (2006.01)
*B01J 37/00* (2006.01)
*C07C 29/145* (2006.01)
*B01J 35/00* (2006.01)
*B01J 35/02* (2006.01)
*C01B 39/42* (2006.01)
*C07C 45/53* (2006.01)
*C07C 409/10* (2006.01)

(52) U.S. Cl.
CPC ........... *C07C 2/864* (2013.01); *B01J 29/7034* (2013.01); *B01J 35/002* (2013.01); *B01J 35/026* (2013.01); *B01J 35/108* (2013.01); *B01J 35/1019* (2013.01); *B01J 35/1038* (2013.01); *B01J 35/1061* (2013.01); *B01J 37/0009* (2013.01); *C01B 39/42* (2013.01); *C07C 2/66* (2013.01); *C07C 29/145* (2013.01); *C07C 45/53* (2013.01); *C07C 409/10* (2013.01); *B01J 2229/42* (2013.01); *C07C 2523/02* (2013.01); *C07C 2523/04* (2013.01); *C07C 2529/70* (2013.01); *Y02P 20/52* (2015.11)

(58) Field of Classification Search
CPC ......... C07C 2/66; C07C 2/864; C07C 15/073; C07C 15/085; C07C 29/145; C07C 31/10; C07C 2523/02; C07C 2523/04; C07C 2529/70; C07C 409/10; C07C 45/53; B01J 2229/42; B01J 29/7034; B01J 35/002; B01J 35/026; B01J 35/1019; B01J 35/1038; B01J 35/1061; B01J 35/108; B01J 37/0009
See application file for complete search history.

(56) References Cited

U.S. PATENT DOCUMENTS

| | | |
|---|---|---|
| 5,015,786 A | 5/1991 | Araki et al. |
| 6,147,270 A | 11/2000 | Pazzucconi et al. |
| 6,872,859 B2 | 3/2005 | Perego et al. |
| 9,259,722 B2 * | 2/2016 | Birkhoff ................. C07C 2/864 |
| 2002/0072467 A1 | 6/2002 | Ogawa |
| 2003/0069459 A1 | 4/2003 | Girotti et al. |

(Continued)

FOREIGN PATENT DOCUMENTS

| | | |
|---|---|---|
| CN | 101690897 A | 4/2010 |
| CN | 102958870 A | 3/2013 |

(Continued)

OTHER PUBLICATIONS

Written Opinion dated Mar. 14, 2017 in Singaporean Patent Application No. 11201602717T.

(Continued)

*Primary Examiner* — Sharon Pregler
(74) *Attorney, Agent, or Firm* — Oblon, McClelland, Maier & Neustadt, L.L.P.

(57) ABSTRACT

The invention relates to a new catalytic composition for the alkylation of aromatic compounds with alcohols, or mixtures of alcohols and corresponding olefins, wherein said composition comprises a zeolite of the MTW type and is characterized in that it contains one or more alkaline metals in a total quantity which is less than or equal to 0.02% by weight. The use of said catalyst in the alkylation of aromatic compounds with alcohols, in particular benzene with isopropanol or ethanol, allows the formation, as by-product, of the aldehyde or ketone corresponding to the alcohol used, to be minimized: the formation of reaction by-products of said aldehydes or ketones having a boiling point very close to that of polyalkylation products, is therefore significantly reduced. This provides a considerable advantage in the subsequent transalkylation step for the recovery of said polyalkylates by transformation into the corresponding monoalkylates.

17 Claims, No Drawings

(56) References Cited

U.S. PATENT DOCUMENTS

| | | | |
|---|---|---|---|
| 2003/0144564 A1 | 7/2003 | Pazzuconi et al. | |
| 2004/0171888 A1 | 9/2004 | Perego et al. | |
| 2006/0122445 A1 | 6/2006 | Pazzuconi et al. | |
| 2007/0191658 A1 | 8/2007 | Lai et al. | |
| 2008/0035525 A1* | 2/2008 | Burgfels | B01J 29/7034 |
| | | | 208/26 |
| 2014/0206909 A1 | 7/2014 | Calaresu et al. | |

FOREIGN PATENT DOCUMENTS

| | | |
|---|---|---|
| EP | 1 192 993 A1 | 4/2002 |
| EP | 2 047 906 A1 | 4/2009 |
| JP | 2002-102714 A | 4/2002 |
| JP | 2007-534578 A | 11/2007 |
| JP | 2009-90285 A | 4/2009 |
| RU | 2 141 934 C1 | 11/1999 |
| WO | WO 2010/029405 A2 | 3/2010 |
| WO | WO 2012/175601 A1 | 12/2012 |
| WO | WO 2012/175614 A1 | 12/2012 |

OTHER PUBLICATIONS

International Search Report dated Jan. 26, 2015 in PCT/IB2014/065296.
Written Opinion dated Jan. 26, 2015 in PCT/IB2014/065296.
International Preliminary Report on Patentability dated Feb. 3, 2016 in PCT/IB2014/065296.
Combined Chinese Office Action and Search Report dated Feb. 21, 2017 in Patent Application No. 201480055498.X (with English translation).
Combined Office Action and Search Report dated Sep. 1, 2017 in Chinese Patent Application No. 201480055498.X (with English language translation).
Office Action dated Apr. 23, 2018 in Japanese Patent Application No. 2016-521779 (with English language translation), 7 pages.
Combined Russian Office Action and Search Report dated May 16, 2018 in Patent Application No. 2016114420/04(022625) (with English language translation), 15 pages.

* cited by examiner

CATALYTIC COMPOSITION AND PROCESS USING IT FOR THE ALKYLATION OF AROMATIC HYDROCARBONS WITH ALCOHOLS, OR MIXTURES OF ALCOHOLS AND OLEFINS

The invention relates to a new catalytic composition for the alkylation of aromatic hydrocarbons with alcohols or mixtures of alcohols and corresponding olefins, wherein said composition comprises a zeolite of the MTW type and is characterized in that it has a suitable and calibrated content of one or more alkaline metals.

The use of said composition in the alkylation of aromatic hydrocarbons with alcohols allows the formation, as by-product, of the aldehyde or ketone corresponding to the alcohol used, to be minimized: the formation of reaction by-products of said aldehydes or ketones is therefore significantly reduced, where said products have a boiling point very close to that of polyalkylation products, and are capable of causing poisoning of the catalyst in the subsequent transalkylation step for the recovery of said polyalkylates.

Catalysts based on phosphoric acid and diatomaceous earth for fixed-bed reactors or $ALCl_3$ in slurry, are still partially used in the petrochemical industry, in addition to zeolitic catalysts, in the alkylation reaction of aromatics with olefins. In all cases, the alkylation reaction of benzene with propylene is carried out under reaction conditions corresponding to the complete liquid phase of the reagent mixture. Problems relating to environmental impact and safety are however linked to processes based on the use of catalysts based on phosphoric acid and $AlCl_3$.

The preparation of cumene using zeolite X or zeolite Y as catalyst, was described for the first time in 1965 (Fnachev, Kr. M., et al, Nefiekhimiya 5 (1965) 676).

The use of zeolites having a faujasitic structure for the alkylation of benzene with light olefins such as propylene, was subsequently described by Venuto et al. (J. Catal. 5, (1966) 81).

Excellent results, in terms of industrial application, were obtained in the synthesis of cumene using zeolites with a beta-type structure, as described in EP 432814, and in particular using catalysts comprising beta zeolites, according to what is described in EP 687500.

Once obtained, cumene is transformed into phenol by means of an oxidation step to cumyl-hydroperoxide, followed by an acid treatment step which causes the breakage of the peroxide bond with the formation of phenol and acetone.

If, on the one hand, the simultaneous production of phenol and acetone in a single production unit certainly represents a positive aspect from an industrial point of view, the existence of an imbalance in the commercial demand for the two products can, on the other hand, represent a problem for the management of the industrial plant for the production of phenol. It should in fact be remembered that for each kg of phenol produced from cumene according to the industrial process via propylene, 0.61 kg of acetone are also obtained.

Considering that one of the major uses of acetone is represented by methylmethacrylate (MMA) whose market demand is decreasing, whereas the demand for bisphenol A (BPA), phenolic resins and caprolactam, main uses downstream of the phenol, is increasing, the potential problem deriving from the coproduction of acetone in the production process of phenol via cumene, can be clearly understood.

U.S. Pat. No. 5,017,729 describes a process for the production of phenol via cumene hydroperoxide characterized by the use of propylene, in the preparation step of cumene, wherein said propylene either totally or partially derives from the reduction of acetone (coproduced with phenol) with hydrogen and subsequent dehydration of isopropyl alcohol.

The considerably onerous nature of the various steps destined for the re-production of pure propylene—to be used in the alkylation step—starting from acetone coproduced with phenol, is evident in this process. In particular, in the process proposed by Mitsui (PEP Review 95-1-1 1) for the production of propylene starting from acetone, the main onerousness of the investment is attributable to the dehydration section of isopropyl alcohol—obtained from acetone in the relative reduction section with hydrogen—to propylene. The dehydration step of IPA to propylene, on the other hand, is necessary for a concrete industrial application, due to the extreme difficulty of carrying out the alkylation of benzene directly with isopropyl alcohol as alkylating agent when acid catalysts of the conventional type are used, due to the water released by the IPA during the reaction, which produces negative effects on the performances of the catalyst in terms of selectivity, but above all, with respect to the duration of the catalyst itself. Acid catalysts, of both the zeolitic and non-zeolitic type, are in fact negatively influenced by the presence of the water developed when isopropyl alcohol is used as alkylating agent of benzene to give cumene.

A process is described in EP 1069100 for the alkylation of benzene with isopropanol, possibly mixed with propylene, which consists in carrying out said reaction under mixed gas-liquid phase conditions or under completely liquid phase conditions, at such temperatures and pressures that the water concentration in the liquid phase of the reaction does not exceed 8,000 ppm w/w, regardless of the total water content in the reaction mixture. The catalyst is of the zeolitic type and preferably selected from beta zeolite, Y, ZSM-12 and mordenite type.

A process is described in EP 1069099 for the alkylation of benzene with isopropanol, or mixtures of isopropanol and propylene, under pressure and temperature conditions corresponding to a complete gas phase of the mixture present in the reaction section and in the presence of a catalyst comprising beta zeolite and an inorganic binder.

Patent application EP 2328852 describes a process for the alkylation of benzene with isopropanol, or a mixture of isopropanol and propylene, which comprises carrying out said alkylation reaction under temperature and pressure conditions corresponding to a complete gas phase of the reagents and in the presence of a catalytic system containing a zeolite belonging to the MTW family.

WO2012175614 describes a process for the alkylation of aromatic hydrocarbons by means of aliphatic alcohols containing from 1 to 8 carbon atoms, which comprises feeding the hydrocarbon and alcohol to the head of a fixed-bed reactor, operating with a "trickle flow" regime, containing at least one layer of a catalyst comprising a zeolite selected from medium-pore zeolites and large-pore zeolites.

In the alkylation of aromatic compounds with alcohols in the presence of MTW zeolites, silica/alumina ratios in the zeolite lattice with values of around 100 are generally used.

The alkylation reaction of benzene with an alkylating agent, whether it be olefin or alcohol, requires an acid catalysis and consequently the zeolite catalysts used in this type of process must be in acid form, i.e. the negative charges present on the crystalline lattice of the zeolite must be neutralized by $H^+$ ions. In order to obtain said zeolites in acid form, sufficient for making them active in the alkylation process of aromatics with olefins or alcohol, the zeolite deriving from the synthesis, which is generally in sodium or potassium form, must be exchanged with $NH_4^+$ ions, and the resulting zeolite in ammonia form must be subjected to calcination: the decomposition of the $NH_4^+$ ions is obtained, with the formation of zeolite in acid form, in which the anionic sites, due to the presence of trivalent metals in the crystalline lattice of the zeolite, are neutralized by $H^+$ ions.

Experts in the field, however, know that commercially available zeolites in any case contain residues of alkaline ions. ZSM-5, Beta, Y zeolites commercially available, for example, typically have a content of alkaline metals, particularly sodium, expressed as $Na_2O$, of 0.05% by weight, commercial products with a lower content and in any case not lower than 0.03%, are rarely found. These data can be easily found in catalogues and websites of the largest zeolite producers. These residues are the result of the balance between two aspects:

the number of ion exchanges, that can be effected consecutively, to which the zeolite can be subjected, in order to eliminate the ions of alkaline metals, but wherein each ion exchange used is onerous from an economic point of view.

the fact that, in any case, the number of acid equivalents available in the final catalyst for the alkylation reaction, does not vary significantly over a certain number of exchanges.

It is therefore evident that currently, on the basis of the knowledge of experts in the field, there does not seem to be any reason for increasing the number of exchanges in order to fall, in commercial catalysts, below the present content limits of alkaline metals.

During the alkylation process of aromatics with alcohols, the problem arises of the undesired formation of the ketone or aldehyde corresponding to the alcohol used: in the alkylation reaction of benzene with isopropanol, for example, there is the problem of the formation of acetone, due to the dehydrogenation of isopropanol. As a result of the acid catalyst, the acetone, in turn, undergoes a series of consecutive reactions which lead to the formation of by-products such as acetophenone and trimethylindenes which have boiling points close to those of diisopropylbenzenes, from which they cannot therefore be easily separated.

The diisopropylbenzenes produced in the alkylation process, after recovery from the reaction effluent, must necessarily be subjected to a transalkylation step with benzene to obtain further cumene and thus improve the material specification of the process.

The by-products mentioned above, in particular acetophenone and trimethylindenes in the case of alkylation with isopropanol, are then fed together with the diisopropylbenzenes to the transalkylation catalyst, normally based on beta or Y zeolite, and are stably absorbed on the acid sites promoting the formation of coke which causes a premature deactivation of the catalyst.

The formation of aldehyde or ketone corresponding to the alcohol used, therefore represents a significant problem in the alkylation of aromatics with alcohols, and it is consequently desirable to find a solution which minimizes their formation: this would lead to a considerable improvement in the performances and stability of the catalyst in the subsequent transalkylation step of diisopropylbenzenes.

The Applicant has now unexpectedly found that these undesired side-reactions forming aldehydes or ketones are favoured by the presence of sodium and/or potassium impurities which, although minimum, catalyze the transformation of alcohols into the corresponding carbonyl compounds by means of basic-type catalysis, thus influencing the economy of the process. The presence of said impurities, as indicated above, is the result of normal procedures for the preparation of zeolite catalysts, known in the art and also used on an industrial scale for the preparation of zeolite catalysts in acid form.

The Applicant has now found that the use in said alkylation process of a catalytic composition containing a MTW zeolite and having a limited and controlled content of ions of alkaline metals, in particular Na and/or K, allows the formation of aldehydes or ketones, corresponding to the alcohol used as alkylating agent, to be minimized, consequently also minimizing the formation of by-products having a boiling point very close to that of polyalkylation products.

The alkylation process of aromatics with alcohols in the presence of the catalytic composition of the present invention, keeps its characteristics relating to the absence of negative effects on performances and the duration of the catalyst, due to the presence of a high water content in the reaction mixture, unaltered maintaining a very high productivity.

The present invention also relates to a process for the preparation of phenol, in which the first step for the preparation of cumene is effected by alkylation of benzene with isopropanol using the new catalyst of the present invention.

Cumene is an important precursor for the preparation of phenol, in turn useful as intermediate in the preparation of caprolactam from which nylon is produced.

The complete process for the preparation of phenol comprises the alkylation of benzene with isopropanol to cumene, the oxidation of cumene to the corresponding hydroperoxide which, by acid treatment, generates phenol.

A first object of the present invention therefore relates to a catalytic composition containing:
  a zeolite of the MTW type,
  one or more alkaline metals in a total amount lower than or equal to 0.02 by weight.

The total amount by weight of alkaline metals is preferably equal to or less than 0.015%, even more preferably equal to or less than 0.01% by weight.

The alkaline metal(s) are present in the form of ions, in particular cations.

Total amount means the amount of alkaline metal, when the composition contains only one metal, or the sum of the amounts of alkaline metals when two or more are present.

A preferred aspect is that the catalytic composition contains only sodium as alkaline metal. According to another preferred aspect, the catalytic composition of the present invention contains only potassium as alkaline metal. A third preferred aspect is that the catalytic composition of the present invention contains both sodium and potassium as alkaline metals.

A preferred aspect is that the $SiO_2/Al_2O_3$ molar ratio in the zeolite is lower than or equal to 95 when the composition contains only sodium as alkaline metal.

Another preferred aspect of the present invention is that the $SiO_2/Al_2O_3$ molar ratio in the zeolite is lower than or equal to 95, whatever the alkaline metal(s) may be, particularly when the composition contains sodium alone, as described above, or potassium alone, or a mixture of sodium and potassium.

The catalytic composition of the present invention preferably contains one or more alkaline metals selected from sodium, potassium or mixtures thereof.

In particular, compositions containing a MTW zeolite and sodium in a quantity ranging from 5 to 40 ppm, and/or K in a quantity ranging from 5 to 80 ppm, preferably ranging from 5 to 40 ppm, are a preferred aspect.

Zeolites of the MTW structural type which can be used are zeolites ZSM-12, CZH-5, Nu-13, Theta-3 or TPZ-12. ZSM-12 zeolite is preferably used.

CZH-5 zeolite is described in GB 2079735A; Nu-13 zeolite is described in EP59059; Theta-3 zeolite is described in EP 162719 and TPZ-12 zeolite in U.S. Pat. No. 4,557,919.

Zeolites of the MTW structural type which are preferably used for preparing the catalyst of the present invention, are silico-aluminates having a $SiO_2/Al_2O_3$ molar ratio higher than or equal to 20. These zeolites are described in A Katovic and G. Giordano, Chem. Ind. (Dekker) (Synthesis of Porous Materials) 1997 69, 127-137. The aluminum can be totally or partially substituted by B, Ga, Fe or mixtures thereof, as described by Toktarev & Ione, in Chon et al., Progress in Zeolites and Microporous Material, SSSC, vol. 105, 1997. ZSM-12 zeolite is described in U.S. Pat. No. 3,832,449, in Ernst et al., Zeolites, 1987, Vol. 7, September, and in Toktarev & Ione, Chon et al., Progress in Zeolites and Microporous Material, SSSC, Vol. 105, 1997.

A further particularly preferred aspect is that the catalyst of the present invention contains a MTW zeolite, in particular ZSM-12 zeolite and, as alkaline metals, Na and/or K ions, each in amounts ranging from 5 to 30 ppm, even more preferably from 10 to 30.

The catalyst of the present invention can contain a binder. The binder is inorganic and can be, for example, alumina, silica, a silicoaluminate, titania, zirconia or clay. The binder is preferably alumina. In the bound catalyst, the zeolite and binder can be in a weight ratio ranging from 5/95 to 95/5, preferably from 20/80 to 80/20. In a preferred embodiment, the end-catalyst is also characterized by particular extrazeolitic porosity characteristics, i.e. the porosity fraction of the catalyst which cannot be attributed to the quality and quantity of the zeolite present in the end-catalyst. In particular, said extrazeolitic porosity has values not lower than 0.4 ml/g of end-catalyst, wherein said extrazeolitic porosity is composed for a fraction of at least 30%, preferably at least 50%, of pores having a diameter larger than 100 Å. Said extrazeolitic porosity, i.e. the porosity fraction of the catalyst which cannot be attributed to the quality and quantity of the zeolite present in the end-catalyst can be obtained by conventional methods, well-known to experts in the field, and is correctly determined according to the known methods described, for example, in U.S. Pat. No. 8,207,388.

The binder used, and any additional component adopted in the formulation and forming operations, can, in turn, contain impurities of alkaline metal ions, in particular sodium and/or potassium: as, in this case, the content of alkaline ions, in particular sodium and/or potassium, of the end-catalyst is also determined by the contribution of the content of alkaline metals of the binder, this contribution must be such that the final content of alkaline metal ions, in particular Na and/or K, in the catalyst is, in any case, lower than 0.02 by weight.

According to a first preferred aspect of the present invention, the catalytic composition comprises a MTW zeolite, preferably a ZSM-12 zeolite, in acid form, wherein the cationic sites present in its structure are occupied by ions of one or more alkaline metal(s) in a total amount lower than or equal to 0.02% by weight, the remaining cationic sites being occupied by $H^+$ ions.

The $SiO_2/Al_2O_3$ molar ratio is preferably lower than or equal to 95, when the composition contains sodium alone as alkaline metal.

According to a further aspect of the invention, in the catalyst, the MTW zeolite can be in bound form with a binder.

According to a third aspect of the invention, said zeolite can be in bound form with a binder, wherein said binder can, in turn, contain ions of one or more alkaline metals, particularly sodium and/or potassium ions: in this case, the overall content of alkaline ions which is lower than or equal to 0.02% by weight, will be the result of the contributions of the content of these ions in the MTW zeolite and of the content of said ions in the binder.

With respect to the first preferred aspect of the present invention indicated above, the catalyst can be in particular a ZSM-12 zeolite having, in its calcined and anhydrous form, a molar composition of the oxides corresponding to the following formula:

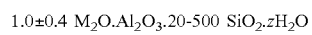

$$1.0 \pm 0.4 \ M_2O.Al_2O_3.20\text{-}500 \ SiO_2.zH_2O$$

wherein z ranges from 0 to 60,

M is $H^+$ and one or more alkaline metal ions, preferably selected from Na and K ions, and mixtures thereof, in a total amount lower than 0.02% by weight, and preferably the $SiO_2/Al_2O_3$ molar ratio is 20-95 when the composition contains only sodium as alkaline metal.

Said zeolite can be in bound form with a binder.

In particular, said zeolite can be in bound form with a binder, wherein said binder can, in turn, contain one or more alkaline metal(s), particularly sodium and/or potassium ions: in this case, the content of alkaline ions lower than or equal to 0.02% by weight will be the result of the contributions of the content of said ions in the MTW zeolite and of the content of said ions in the binder. Any component additionally used in the formulation and forming operations containing impurities of alkaline metals, in turn, contributes to their final content in the composition formed.

When the catalyst of the present invention contains a binder, a particularly preferred aspect is that said catalyst is in the form of pellets having a diameter ranging from 1.5 to 5 mm and a length ranging from 1 to 50 mm, with a hardness greater than or equal to 8 kg. Pellets having a diameter ranging from 1.5 to 3 mm are preferred. The length of the pellets preferably varies from 2 to 40, even more preferably from 4 to 30. A hardness greater than or equal to 9 kg, even more preferably greater than 10 kg, is preferred.

The catalyst of the present invention is prepared from MTW zeolite in the form directly deriving from the synthesis with suitable and calibrated ion exchanges in order to reach the desired content of alkaline metal ions, particularly Na and/or K, in the end-catalyst.

The MTW zeolite deriving directly from the synthesis, will have the cationic sites substantially occupied by ions or one or more alkaline metal(s), in particular Na and/or K, according to the preparation process and reagents used.

Said zeolite in cationic form is subjected to a number of exchanges which is such as to reach the quantity of residual content of ions of alkaline metals, in particular Na and/or K, according to the invention. Said exchanges will be effected using methods used in the art, the exchange is effected, for example, with an aqueous solution of ammonium salts, ammonium acetate, for example, and subsequent final thermal treatment in order to decompose the ammonia form of the zeolite and transform it into the proton form. Ion exchange methods that can be used for preparing the catalysts of the present invention are described, for example, in Townsend R. P. (1991) Ion Exchange in Zeolites, in van Bekkum, E M Flanigen and J C Jansen eds. Introduction to Zeolite Science and Practice, Stud. Surf. Sci. Catal. Volume 58, pages 359-390 (Elsevier), and in Townsend R. P., Harjula R. (2002) Ion exchange in molecular sieves by conventional techniques, in H. G. Karge and J. Weitkamps eds. Post-synthesis modification I, pages 1-42 (Springer, Berlin/Heidelberg).

Said ion exchanges can be repeated, possibly combined with thermal treatment.

The Applicant has found that by using the catalytic composition of the present invention, with a reduced content of cations of alkaline metals, it is possible to obtain the alkylation of aromatic hydrocarbons with alcohols by means of a process which, in addition to providing optimum results in terms of performances, duration of the catalyst and therefore productivity, unexpectedly leads to a reduced formation of aldehydes or ketones corresponding to the alcohols used, consequently minimizing the formation of by-products having boiling points close to those of poly-alkylation products: this is reflected in the subsequent transalkylation step in which the reduced presence of these by-products causes a much lower deactivation of the transalkylation catalyst.

An object of the present invention therefore relates to a process for the alkylation of aromatic hydrocarbons with alcohols, or mixtures of the alcohol used and the corresponding olefin, which comprises effecting said alkylation reaction in the presence of a catalyst containing:
 a zeolite of the MTW type,
 one or more alkaline metals in a total amount lower than 0.02% by weight.

A particularly preferred aspect is that the $SiO_2/Al_2O_3$ molar ratio in the zeolite is lower than or equal to 95 when the composition contains sodium alone as alkaline metal.

Benzene or toluene is preferably used as aromatic hydrocarbon, benzene is even more preferred.

An aliphatic alcohol containing from 1 to 8 carbon atoms is preferably used as alcohol, even more preferably ethyl alcohol, iso-propyl alcohol, n-propyl alcohol, n-butyl alcohol, iso-butyl alcohol, sec-butyl alcohol, t-butyl alcohol.

The aromatic compound is preferably benzene and the alcohol is selected from ethanol and iso-propanol.

The alcohol can be used in a mixture with the corresponding olefin. In particular, ethanol can be used in a mixture with ethylene and isopropanol can be used in a mixture with propylene.

The reaction can be carried out in gas phase, mixed phase or liquid phase.

The reaction conditions preferably correspond to a complete gas phase of the reagents, i.e. operating under pressure and temperature conditions which are such as to have the reagents present exclusively in gas phase.

According to an aspect of the present invention, it is possible to operate under pressure and temperature conditions which also correspond to a complete gas phase of all the mixture present in the reaction section: in this case therefore, not only the reagents, but also the products, are in gas phase.

According to another aspect of the present invention, temperature and pressure conditions can be selected, which correspond also to at least partial liquid phase of the reaction products: in this case therefore, the reagents are in gas phase, whereas the products are, at least partially, liquid.

According to a preferred aspect of the process of the present invention, it is possible to operate at a reaction temperature ranging from 150° C. to 230° C., at a reaction pressure ranging from 1 to 20 bar. It is preferable to operate at such conditions as to have the reagents present in completely gaseous phase and indifferently using alcohol or mixtures of alcohol with the corresponding olefin as alkylating agent.

It is preferable to operate at a pressure lower than 10 bar, preferably ranging from 5 to 9 bar.

The molar ratio between aromatic compound and alcohol preferably ranges from 2 to 10, even more preferably from 2 to 4.

When an olefin is also additionally used as alkylating agent together with the corresponding alcohol, the molar ratio between aromatic compound and alkylating agent, alcohol plus olefin, preferably ranges from 2 to 10, more preferably from 2 to 4. The molar ratio between alcohol and olefin preferably ranges from 10 to 0.01, even more preferably from 5 to 0.1.

The alkylation of the aromatic hydrocarbon, according to the process of the present invention, can be carried out in continuous, semi-continuous or batchwise.

When the process is carried out in continuous, it is possible to also operate using a configuration of the reaction system which envisages partial recycling, to the reaction section, of the organic phase of the effluent leaving the same reaction section, after cooling, demixing and removal of the aqueous phase from the organic phase.

According to a preferred aspect of the present invention, the alkylation process is effected under "trickle flow" conditions, as described in patent application WO2012/175614.

A particular object of the present invention therefore relates to an alkylation process of aromatic hydrocarbons by means of aliphatic alcohols containing from 1 to 8 carbon atoms, which comprises feeding the hydrocarbon and the alcohol to the head of a fixed-bed reactor, operating under "trickle flow" regime, containing at least one layer of catalyst comprising:
 a zeolite of the MTW type,
 one or more alkaline metals in a total amount lower than 0.02% by weight.

In particular, said process, carried out in continuous, comprises:
(a) mixing, in liquid phase, at least one aromatic hydrocarbon (A), the alcohol containing from 1 to 8 carbon atoms (B), and a recycled stream (C) coming from a discharge section of the alkylation reactor;
(b) feeding the mixture obtained in step (a), preheated to the reaction temperature, to the head of a fixed-bed alkylation reactor, operating under "trickle flow" regime, containing at least one layer of a catalyst, containing:
 a zeolite of the MTW type,
 one or more alkaline metal(s) in a total amount lower than 0.02% by weight;
(c) cooling the reaction mixture in a discharge section, in order to obtain an organic phase, comprising the alkylated aromatic hydrocarbon, and an aqueous phase essentially consisting of reaction water,
(d) dividing the organic phase into a recycled stream (C), sent to the head of the alkylation reactor for the mixing phase with the reagents, and a final stream, comprising the alkylated aromatic hydrocarbon.

A further preferred aspect of the present invention relates to a continuous process for the alkylation of aromatic hydrocarbons by means of $C_1$-$C_8$ aliphatic alcohols in a fixed-bed alkylation reactor comprising:
(a) mixing, in liquid phase, at least one aromatic hydrocarbon (A) and the $C_1$-$C_8$ alcohol (B) with molar ratios A/B higher than 1, preferably ranging from 1.5 to 5;
(b) diluting the mixture coming from step (a) with a recycled stream coming from a discharge section of the alkylation reactor, so as to have a recycled weight ratio C/AB between the recycled stream (C) and the reagent mixture (AB) ranging from 1.5:1 to 10:1;

(c) feeding the final mixture obtained, pre-heated to the reaction temperature, to the head of a fixed-bed alkylation reactor, operating under "trickle flow" regime, containing at least one layer of a catalyst containing:
   a zeolite of the MTW type,
   one or more alkaline metals in an overall amount lower than 0.02% by weight, (d) cooling the reaction mixture, directly downstream of the alkylation reactor, in a discharge section, in order to obtain an organic phase, comprising the alkylated aromatic hydrocarbon and an aqueous phase essentially consisting of reaction water;

(e) dividing the organic phase into a recycled stream (C) sent to the head of the alkylation reactor for the mixing phase with the reagents and a final stream comprising the alkylated aromatic hydrocarbon.

The final stream thus obtained can then be sent to subsequent process phases such as transalkylation.

The flow-rate of the reagents to the alkylation reactor is such as to provide a WHSV (Weight Hourly Space Velocity) ranging from 1 to 8 hours$^{-1}$, for example, and preferably from 2 to 6 hours$^{-1}$.

The regime of the "trickle flow" type is preferably obtained by managing the operative conditions of the alkylation reactor so as to have a gaseous phase essentially consisting of the reagents, and a liquid phase essentially consisting of the alkylation product, i.e. the monoalkylated aromatic hydrocarbon and possibly polyalkylated hydrocarbons.

The water, which is in turn formed by the reaction, is distributed between the gaseous phase and liquid phase, and is prevalently in gas phase.

Inside the alkylation reactor, the reaction temperature preferably ranges from 160 to 250° C., more preferably from 180 to 230° C., with an internal pressure that varies between 1 and 10 MPa, more preferably from to 5 MPa. An expert in the field is capable of selecting, for each aromatic substrate and for each alcohol, the temperature and pressure conditions which create the presence of a gaseous phase and a liquid phase in the alkylation reactor operating in a "trickle flow" regime, in particular, pressure and temperature conditions which make it possible to operate with the reagents that are in gas phase and the products that are in liquid phase. All the aspects described in WO2012/175614 can be applied and used in the process of the present invention.

The objectives of the present invention also include, in particular, a process for preparing phenol comprising the following steps:

1) alkylation of benzene with isopropanol, or a mixture or isopropanol and propylene, to give cumene and water, which comprises effecting said alkylation reaction completely in gaseous phase and in the presence of a catalytic system containing:
   a zeolite of the MTW type,
   one or more alkaline metal(s) in an overall amount lower than 0.02% by weight;
2) oxidation of the cumene thus obtained to cumyl hydroperoxide;
3) treatment of the cumyl hydroperoxide with acids in order to obtain a mixture of phenol and acetone;
4) hydrogenation of acetone to isopropanol which is recycled to step (1).

Step (1) is carried out according to the aspects indicated above of the alkylation process of the present invention, comprising the particular embodiment using a "trickle flow" regime described above. In step (2), the cumene deriving from step (1) is oxidized with air to give cumyl hydroperoxide which is in turn treated with an acid to give a mixture of phenol and acetone which is fractionated to separate the phenol from the acetone. In step (3) the acetone obtained in step (2) is partly or totally hydrogenated to isopropyl alcohol which is recycled to step (1).

According to a preferred aspect, at the end of the first step, after separating, by fractionation, the desired product, cumene, which passes to the subsequent oxidation step, the remaining fraction of polyisopropylbenzenes is used in a separate step for a transalkylation reaction with benzene to recover further cumene.

The transalkylation reaction can be carried out using any of the catalysts known to experts in the field for the transalkylation of polyisopropylbenzenes with benzene, in particular, it can be conveniently carried out in the presence of beta zeolite or a catalyst based on beta zeolite, in particular, prepared according to what is described in EP 687500 and EP 847802. The temperature conditions for the transalkylation reaction can be selected from 100° C. to 350° C., the pressure is selected from 10 to 50 atm and the WHSV from 0.1 hr$^{-1}$ to 200 hr$^{-1}$.

In accordance with the present invention, the catalyst used in the transalkylation step maintains its activity for a longer period of time, as it is not poisoned by the typical by-products of alkylation, effected in accordance with the prior art, in which there is the formation of condensation products of the carbonyl compounds formed from the alcohols used as alkylating agents.

In step (2) the cumene deriving from step (1), and possibly from the transalkylation step, is oxidized to cumyl hydroperoxide. The cumyl hydroperoxide is then transformed into phenol and acetone. The oxidation to cumyl hydroperoxide and the subsequent transformation into phenol, can be effected, for example, as described in U.S. Pat. No. 5,017,729. In the last step, part or all of the acetone obtained as by-product from step (2), is hydrogenated to isopropyl alcohol which is re-fed to the initial step.

The following examples are provided for illustrating the invention claimed herein without limiting its objectives in any way.

EXAMPLE 1 (ACCORDING TO THE INVENTION)

150 g of ZSM-12 ZD06047 zeolite powder (Zeolyst) having a $SiO_2/Al_2O_3$ molar ratio equal to 65, containing 0.01% by weight of Na and 0.03% by weight of K, are subjected to ion exchange for 1 hour at 60° C. with a solution obtained by dissolving 150 g of ammonium acetate in 1,800 ml of water.

The product thus obtained is washed 3 times with 1.5 liters of water, and subsequently dried at 120° C. for at least 2 hours, obtaining a dried product.

After drying, the zeolite powder is calcined at 580° C. for 4 hours.

122.3 g of ZSM-12 zeolite obtained from the calcination and 132 g of pseudo-bohemite Versal V200 are dry mixed for 4 hours in an Erweka planetary mixer. 190 ml of aqueous solution of acetic acid at 5% are subsequently fed, slowly and under stirring, for 4 hours.

The paste thus obtained is extruded into pellets having a diameter of 2 mm and a length of 10 mm, which are left to age for 2 days in the atmosphere.

At the end of the aging, the pellets are calcined at 580° C. for 4 hours.

An extruded catalyst is obtained, with about 55% of active phase, containing:
Na=23 ppm
K=5 ppm
The extruded catalyst has the following characteristics:
Hardness=11.8 kg
Poured density=0.59 g/cc
Pore volume (mercury intrusion)=0.47 cc/g
Pellet density=1.16 g/cc
Surface area (BET)=281 m$^2$/g
A fraction equal to 59% of the extrazeolitic porosity has pores having a diameter higher than 100 Å.

EXAMPLE 2 (ACCORDING TO THE INVENTION)

150 g of the same ZSM-12 ZD06047 zeolite (Zeolyst) used in Example 1 are subjected to ion exchange for 1 hour at 60° C. with a solution obtained by dissolving 150 g of Ammonium Acetate in 1,800 ml of water.

The product thus obtained is washed 3 times with 1.5 liters of water, and subsequently dried at 120° C. for at least 2 hours.

134 g of ZSM-12 zeolite obtained after drying and 145 g of pseudo-bohemite Versal V200 are dry mixed for 4 hours in an Erweka planetary mixer.

205 ml of aqueous solution of acetic acid at 5% are subsequently fed, slowly and under stirring, for 4 hours.

The paste thus obtained is extruded into pellets having a diameter of 2 mm and a length of 10 mm, which are left to age for 2 days in the atmosphere.

At the end of the aging, the pellets are calcined at 580° C. for 4 hours.

An extruded catalyst is obtained, with about 55% of active phase, containing:
Na=28 ppm
K=10 ppm
The extruded catalyst has the following characteristics:
Hardness=12.8 kg
Poured density=0.62 g/cc
Pore volume (mercury intrusion)=0.43 cc/g
Pellet density=1.25 g/cc
Surface area (BET)=280 m$^2$/g
A fraction equal to 56% of the extrazeolitic porosity has pores having a diameter higher than 100 Å.

EXAMPLE 3 (COMPARATIVE)

150 g of powder of the same ZSM-12 ZD06047 zeolite (Zeolyst) used in Example 1 and 162 g of pseudo-bohemite Versal V200 are dry mixed for 4 hours in an Erweka planetary mixer.

200 ml of aqueous solution of acetic acid at 5% are subsequently fed, slowly and under stirring, for 4 hours.

The paste thus obtained is extruded into pellets having a diameter of 2 mm, which are left to age for 2 days in the atmosphere.

At the end of the aging, the pellets are calcined at 580° C. for 4 hours.

An extruded catalyst is obtained, with about 55% of active phase, containing:
Na=80 ppm
K=140 ppm
The extruded catalyst has the following characteristics:
Hardness=9.1 kg
Poured density=0.52 g/cc
Pore volume (mercury intrusion)=0.54 cc/g
Pellet density=1.01 g/cc
Surface area (BET)=278 m$^2$/g
A fraction equal to 64% of the extrazeolitic porosity has pores having a diameter higher than 100 Å.

EXAMPLE 4—CATALYTIC TEST

An alkylation test of benzene is carried out with isopropyl alcohol using the experimental device described hereunder.

The experimental device is composed of tanks for the reagents: benzene and isopropyl alcohol, feeding pumps of the reagents to the reactor, preheating unit of the reagents, steel reactor positioned inside an electric heating oven, regulation loop of the temperature inside the reactor, regulation loop of the pressure inside the reactor, cooling of the reactor effluent and collection system of the liquid and gaseous products.

In particular, the reactor consists of a cylindrical steel tube with a mechanical seal system and diameter equal to about 2 cm. Along the major axis of the reactor, there is a thermowell having a diameter equal to 1 mm in which there is a thermocouple free to slide along the major axis of the reactor.

The catalyst of Example 1 is charged into the reactor. A quantity of inert material is charged above and below the catalytic bed in order to complete it.

The benzene and isopropanol (IPA) reagents are fed to the reactor—preheated and premixed in a specific mixer—with up-flow.

The reaction products are analyzed via gaschromatography. The reaction conditions under which the test is carried out, are the following:
Reaction temperature: 195° C.
Reaction pressure: 5 bar
WHSV: 2 hours$^{-1}$
[Benzene]/[IPA] in the feed: 3.2 moles/moles
The total concentration of water present in the complete conversion system of the isopropyl alcohol reagent is equal to about 5%.

The selectivity during the whole test proves to be equal to 83.6% for the selectivity [Cum]/[IPA] (cumene with respect to the total IPA converted) and 99.0% for the selectivity [Ar]/[IPA] (cumene+diisopropylbenzene+triisopropylbenzene with respect to the total IPA converted).

The specific production of acetone proves to be equal to 0.74 Kg per ton of cumene.

EXAMPLE 5—COMPARATIVE TEST

Example 4 is repeated using the catalyst of Example 3.

The same experimental device used in Example 3 is adopted, under the same operating conditions.

The selectivity during the whole test proves to be equal to 82.1% for the selectivity [Cum]/[IPA] and 98.7% for the selectivity [Ar]/[IPA]. In particular, the specific production of acetone proves to be equal to 2.58 Kg per ton of cumene, consequently over three times higher with respect to that obtained in Example 4 in which a catalyst according to the invention is used.

The invention claimed is:

1. A process for the alkylation of an aromatic hydrocarbon with an aliphatic alcohol having 1-8 carbon atoms, or with a mixture of the aliphatic alcohol having 1-8 carbon atoms and a corresponding olefin, which comprises effecting said alkylation in the presence of a catalytic composition comprising:
   a zeolite of the MTW type,
   5 to 40 ppm of sodium ions, and
   5 to 80 ppm of potassium ions,
   wherein:
   the $SiO_2/Al_2O_3$ molar ratio in said zeolite is 20-95, and
   the total amount of alkaline metals, including sodium ions and potassium ions, in the catalytic composition is lower than or equal to 0.015% by weight with respect to the total weight of the catalytic composition.

2. The process according to claim 1, wherein the zeolite is ZSM-12.

3. The process according to claim 1, wherein said catalytic composition further comprises a binder.

4. The process according to claim 1, wherein said catalytic composition comprises said MTW zeolite in acid form wherein the cationic sites present in its structure are occupied by $Na^+$ and $K^+$ ions and the remaining cationic sites are occupied by $H^+$ ions.

5. The process according to claim 4, wherein the zeolite is a ZSM-12 zeolite, having, in its calcined and anhydrous form, a molar composition of the oxides corresponding to the following formula:

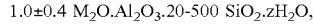

$1.0\pm0.4\ M_2O.Al_2O_3.20\text{-}500\ SiO_2.zH_2O,$ wherein z ranges from 0 to 60, M is $H^+$ and $Na^+$ and $K^+$ ions, in a total amount lower than 0.015% by weight with respect to the total weight of the catalytic composition.

6. The process according to claim 3, wherein said catalytic composition is in the form of a pellet having a diameter ranging from 1.5 to 5 mm and a length ranging from 1 to 50 mm, with a hardness higher than or equal to 8 kg.

7. The process according to claim 3, wherein said catalytic composition has an extrazeolitic porosity not lower than 0.4 ml/g, wherein said extrazeolitic porosity is for at least 30% characterized by pores having a diameter greater than 100 Å.

8. The process according to claim 1, wherein the aromatic hydrocarbon is benzene or toluene.

9. The process according to claim 1, wherein the aliphatic alcohol is ethanol or iso-propanol.

10. The process according to claim 1, carried out in gas phase, mixed phase or liquid phase.

11. The process according to claim 10, carried out under reaction conditions corresponding to a complete gas phase of the reagents.

12. The process according to claim 1, carried out under trickle-flow conditions.

13. The process according to claim 1, wherein the aromatic hydrocarbon is benzene, the aliphatic alcohol is iso-propanol, the alkylation product is cumene and said process further comprises:
   oxidizing the cumene thus obtained to cumyl-hydroperoxide;
   treating the cumyl-hydroperoxide with acids to obtain a mixture of phenol and acetone;
   hydrogenating the acetone to isopropanol which is recycled to the alkylation.

14. The process according to claim 1, wherein the process comprises the alkylation of the aromatic hydrocarbon with the aliphatic alcohol having 1-8 carbon atoms, and not with the mixture of the aliphatic alcohol having 1-8 carbon atoms and the corresponding olefin.

15. The process according to claim 1, wherein the process comprises the alkylation of the aromatic hydrocarbon with the mixture of the aliphatic alcohol having 1-8 carbon atoms and the corresponding olefin.

16. The process according to claim 1, wherein the catalytic composition comprises 5 to 30 ppm of said sodium ions and 5 to 30 ppm of said potassium ions.

17. The process according to claim 1, wherein the aliphatic alcohol having 1-8 carbon atoms is selected from ethyl alcohol, iso-propyl alcohol, n-propyl alcohol, n-butyl alcohol, iso-butyl alcohol, sec-butyl alcohol, and t-butyl alcohol.

* * * * *